United States Patent [19]

Kiyozumi et al.

[11] Patent Number: 4,579,994

[45] Date of Patent: Apr. 1, 1986

[54] PROCESS FOR PREPARING LOWER OLEFIN USING CALCIUM PHOSPHATE MODIFIED ZEOLITE TYPE CATALYST

[75] Inventors: Yoshimichi Kiyozumi; Kunio Suzuki; Shigemitsu Shin; Hideo Okado; Kazumi Noguchi, all of Yatabe, Japan

[73] Assignee: Itaru Todoriki, Japan

[21] Appl. No.: 706,871

[22] Filed: Feb. 28, 1985

[30] Foreign Application Priority Data

Jun. 30, 1984 [JP] Japan .................. 59-135750

[51] Int. Cl.$^4$ ............................. C07C 1/20
[52] U.S. Cl. .................................... 585/640
[58] Field of Search ........................ 585/640

[56] References Cited

U.S. PATENT DOCUMENTS 3,911,041 10/1975 Kaeding et al. .............. 585/640
4,433,189 2/1984 Young ........................... 585/640

Primary Examiner—Curtis R. Davis
Attorney, Agent, or Firm—Birch, Stewart, Kolasch & Birch

[57] ABSTRACT

A process for preparing lower olefin using a calcium phosphate modified zeolite type catalyst is disclosed which is capable of reducing the decomposition of methanol into CO and $CO_2$ and increasing the olefin selectivity. In the process, the reaction of methanol and/or dimethyl ether is carried out in the presence of an aluminosilicate zeolite-type catalyst which has a Ca-containing compound and a P-containing compound contained therein in predetermined amounts.

8 Claims, 6 Drawing Figures

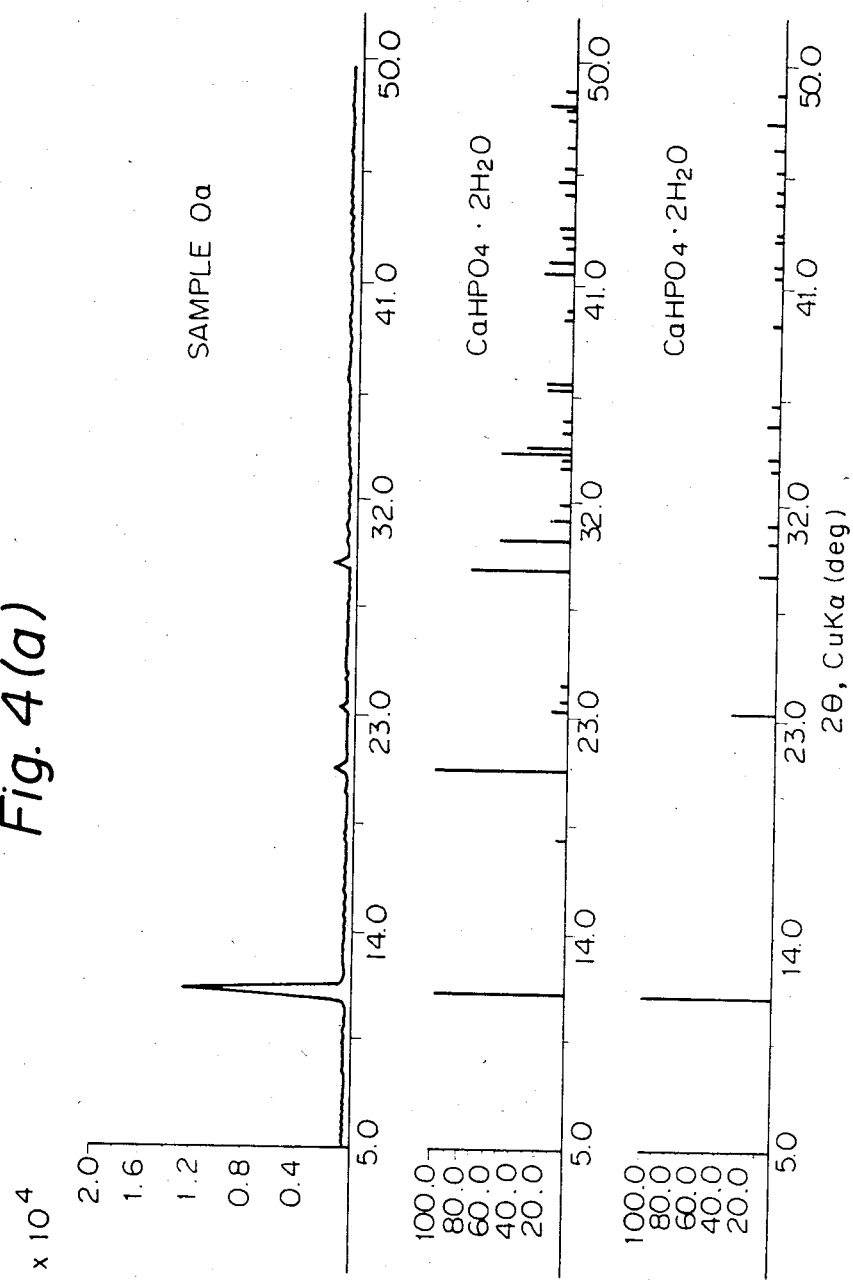

PROCESS FOR PREPARING LOWER OLEFIN USING CALCIUM PHOSPHATE MODIFIED ZEOLITE TYPE CATALYST

BACKGROUND OF THE INVENTION

1. Field of the Invention

This invention generally relates to a process for preparing lower olefin from methanol and/or dimethyl ether, and more particularly to a process for preparing lower olefin from methanol and/or dimethyl ether using an aluminosilicate zeolite-type catalyst in which a calcium-containing compound and a phosphor-containing compound are incorporated.

2. Field of the Invention

Recently, great concern has been shown in the steady supply of petroleum. This is particularly remarkable in Japan because 99% of petroleum consumed in Japan is imported from abroad. In order to overcome such a problem, consideration has been given to the availability of coal, natural gas and the like. In particular, it has been desired to develop an industrial process for synthesizing organic compounds such as olefin, paraffin, an aromatic compound and the like using methanol obtained from methane, CO and the like.

It is widely known in the art that silica-alumina, crystalline aluminosilicate and the like have been conventionally used as a typical catalyst for the conversion of hydrocarbon. Crystalline aluminosilicate possesses a number of pores or fine tunnels of sizes varied depending upon the kind. This causes the aluminosilicate to have shape-selective characteristics of adsorbing, in various kinds of molecules mixed together, only molecules satisfying specific conditions; thus, it is generally called a molecular sieve.

In the 1970s, Mobile Oil Corp. in the United States developed a ZSM-5 type zeolite catalyst as a shape-selective catalyst for preparing hydrocarbon mainly consisting of a high quality gasoline from methanol and/or dimethyl ether. The zeolite has an excellent advantage in that a ratio of $SiO_2/Al_2O_3$ in the composition can be controlled as desired and it has highly improved heat resistance, as compared with conventional zeolite. Also, the zeolite catalyst has satisfactory properties such as a high heat resistance and the like. Further, the catalyst exhibits another advantage capable of converting a main product by the conversion reaction of methanol or dimethyl ether into lower olefin. For example, West-Germany Pat. No. 2935863 discloses that an activation-type zeolite (H-ZSM-5) of which a ratio of $SiO_2/Al_2O_3$ is between 35 and 1600 allows a methanol conversion reaction at a temperature range between 350° C. and 600° C. to produce lower olefin having 2-4 carbon atoms with a yield of up to 70.1 wt.%. Also, the examples of the West-German patent indicate that the optimum ratio of $SiO_2/Al_2O_3$ in the structure of the ZSM-5 type zeolite catalyst and the optimum reaction temperature of the catalyst are 298°-500° and 550° C., respectively. This clearly reveals that the manufacture of hydrocarbon mainly consisting of lower olefin from methanol and/or dimethyl ether is advantageously carried out at a temperature as high as possible. However, the methanol conversion reaction at such a temperature frequently causes the catalytic action of the ZSM-5 type zeolite catalyst to be rapidly deteriorated at a reaction temperature above 550° C., irrespective of its high heat resistance. Accordingly, in order that lower olefin is manufactured from methanol and/or dimethyl ether used as a starting material at a high temperature above 500° C. with a high yield and without causing the rapid deterioration of catalytic action of the zeolite catalyst for a long period of time, it is highly desired to develop a zeolite catalyst which is capable of substantially decreasing the formation of a coke precursor or BTX (benzene, toluene and xylene) and does not readily cause the deterioration of catalytic activity at a temperature above 550° C.

In view of the foregoing, the inventors made efforts to develop a catalyst free of high-temperature deterioration in the conversion reaction of methanol and/or dimethyl ether at a high temperature range above 500° C. which is advantageous to the formation of lower olefin and, as a result, it was found that microcrystalline pentasil-type zeolite, such as ZSM-5, meets such requirements as described above which is synthesized under conditions of strictly controlling time and temperature for crystallization and a ratio of $H_2O/SiO_2$ and has a crystal grain size of the submicron order or below. The zeolite is disclosed in the inventors' earlier Japanese Patent Application Nos. 105537/1984 and 105538/1984 herein incorporated by reference.

Unfortunately, it has been found that even the zeolite catalyst prepared as described above fails to provide a long-term service due to the deterioration of the catalytic action with time.

BRIEF SUMMARY OF THE INVENTION

The present invention has been made in view of the foregoing disadvantage of the prior art and while taking notice of the fact that as a result of the inventors' further efforts to develop a zeolite catalyst which is capable of preventing the deposition of coke thereon and significantly lengthening its life, aluminosilicate zeolite which has suitable amounts of calcium-containing compound and phosphorus-containing compound contained therein is highly useful as a catalyst which is capable of satisfying the above-noted requirements and substantially improving the lower olefin selection characteristics and the yield of the olefin.

In accordance with the present invention, there is provided a process for preparing lower olefin comprising the step of carrying out the reaction of methanol and/or dimethyl ether at a temperature of 300°-700° C. under overall pressure of 0.1-100 normal atmosphere at a weight hourly space velocity of 0.01-20 $hr^{-1}$ at the presence of an aluminosilicate zeolite-type catalyst which has a calcium-containing compound and a phosphorus-containing compound contained therein in the amounts of 0.7 wt.% or more based on Ca and 0.7 wt.% or more based on P, respectively.

Accordingly, it is a primary object of the present invention to provide a process for preparing lower olefin which is capable of substantially reducing the decomposition of a starting material into CO and $CO_2$ and significantly increasing the olefin selectivity.

It is another object of the present invention to provide a process for preparing lower olefin which is capable of substantially reducing the by-production of paraffin and/or an aromatic compound.

It is a further object of the present invention to provide a process for preparing lower olefin which is capable of preventing the deposition of carbon on a catalyst and substantially eliminating a decrease in activity of the catalyst and the deterioration of the catalyst.

Still other objects and advantages of the invention will in part be obvious and will in part be apparent from the specification.

BRIEF DESCRIPTION OF THE DRAWINGS

For a fuller understanding of the invention, reference is had to the following description taken in connection with the accompanying drawings, in which:

FIG. 4(a), 4(b) and 4(c) are charts showing the comparison of X-ray diffraction patterns of as-made calcium phosphate immediately preparation (Sample 0a), dried calcium phosphate (Sample 0b) and calcined calcium phosphate (Sample 0c) (the axis of ordinates indicating diffraction intensity) with bar graphs of X-ray diffraction of $CaHPO_4.2H_2O$, $CaHPO_4$ and $Ca_2P_2O_7$ (the axis of ordinates indicating relative diffraction intensity), respectively.

DETAILED DESCRIPTION OF THE INVENTION

Figure 1:
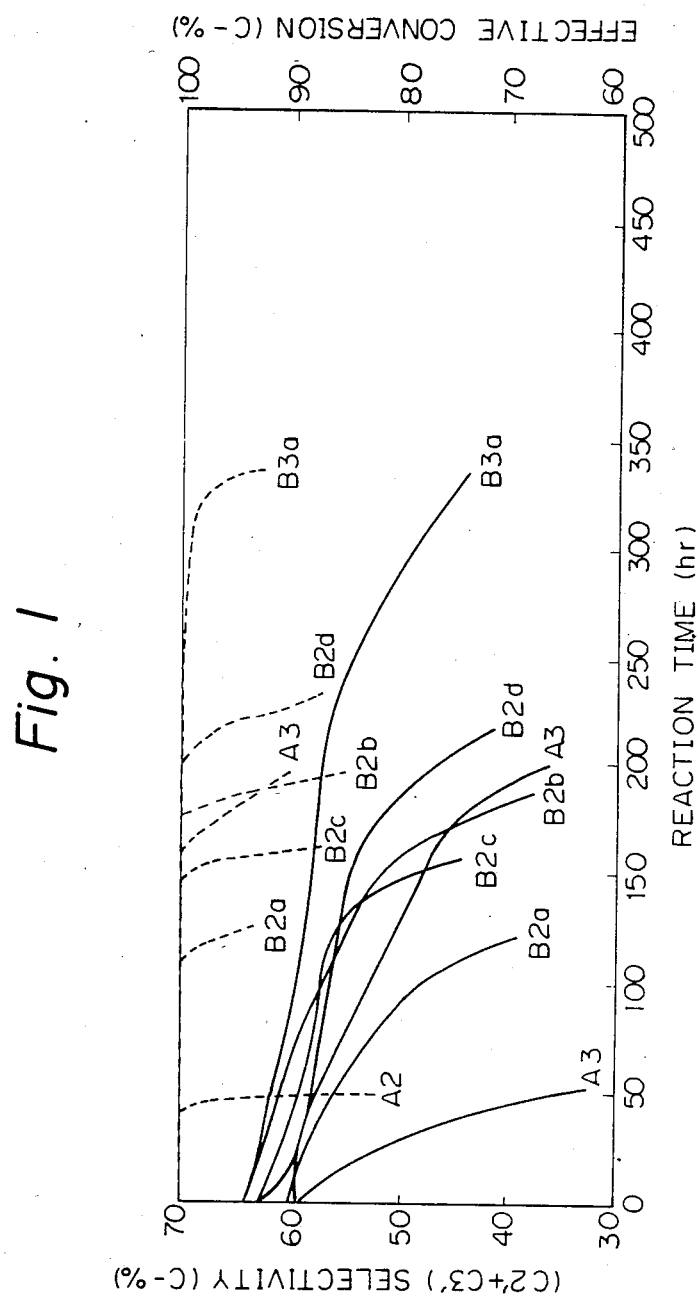
FIG. 1 is a graphical representation showing the variation of ethylene+propylene selectivity [(C2'+C3') selectivity] and the effective conversion of a catalyst with time in each of the methanol conversion reactions at a reaction temperature of 550° C. using catalysts of Samples A2, A3, B2a to B2d and B3a, wherein solid lines indicate the variation of (C2'+C3') selectivity and dotted lines indicate the variation of effective conversion.

The present invention relates to a process for preparing lower olefin comprising the step of carrying out the reaction of methanol and/or dimethyl ehter at a temperature of 300°-700° C. under overall pressure of 0.1-100 normal atmosphere at a weight hourly space velocity of 0.01-20 hr$^{-1}$ at the presence of an aluminosilicate zeolite-type catalyst which has a calcium-containing compound and a phosphorus-containing compound contained therein at levels or in the amounts of 0.7 wt.% or more based on Ca and 0.7 wt.% or more based on P, respectively. As will be described hereinafter, crystalline calcium phosphate hardly exhibits a catalytic action of converting methanol into lower olefin and rather acts as a catalyst poison for a zeolite catalyst which promotes a decomposing methanol into hydrogen, carbon monoxide, carbon dioxide, methane and the like. Nevertheless, a zeolite catalyst containing calcium phosphate has a remarkable advantage of significantly improving the yield of ethylene+propylene as compared with an unmodified zeolite and having a life twice as long as the unmodified zeolite.

Now, the preparation of a zeolite catalyst used in the present invention and the preparation of lower olefin using such a zeolite catalyst will be described in detail. The following description of aluminosilicate zeolite having a calcium-containing compound and a phosphorus-containing compound contained therein will be illustratively made on a microcrystalline ZSM-5 zeolite. However, it should be noted that the present invention is never limited to such a specific zeolite. For example, the present invention may employ any natural and synthetic aluminosilicate zeolites including those wherein the elements of groups I, II and III of the periodic table such as $Be^{2+}$, $Mg^{2+}$, $B^{3+}$, $Ga^{3+}$, $Fe^{3+}$ and the like are substituted for Al to form a solid solution and/or the elements of groups IV and V such as $Ge^{4+}$, $P^{5+}$, $As^{5+}$ and the like are substituted for Si to form a solid solution. Thus, it will be noted that the term "aluminosilicate zeolite-type catalyst" used herein indicates a material having a composition represented by the following formula:

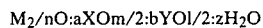

$$M_{2/n}O:aXO_{m/2}:bYO_{l/2}:zH_2O$$

wherein M is a cation; n is a valence of the cation M; X is at least one metal selected from the elements of groups II, III and VIII such as Al, Be, B, Ga, Fe and the like; m is a valence of the metal X; Y is at least one metal selected from the elements of groups IV and V such as Si, Ge, P, As and the like; l is a valence of the metal Y; a and b each are a positive integer; and z is 0 or a positive integer.

The calcium-containing compound suitable for use in the present invention includes various inorganic and/or organic salts of calcium. The carboxylate such as the acetate, the hydroxide, the carbonate, the nitrate and the like are preferably used as the calcium-containing compound. Also, it includes the phosphate, the borate and the like. The phosphorus-containing compound includes various inorganic and/or organic salts of phosphorus. In particular, phosphate, various ammonium hydrogen phosphates and the like are preferably used. Also, it includes condensed phosphate and the like. These calcium-containing compound and phosphorus-containing compound contained in the zeolite may be used in the form of solid. Alternatively, those may be used in the form of suitable solution or slurry.

The incorporation of each of the calcium-containing compound and phosphorus-containing compound into the zeolite may be carried out, for example, by contacting its solution with the zeolite, and subjecting it to evaporation to dryness (impregnation process) or separating the solvent from the solute by filtration or centrifugation (separation process). Various solvents may be used in the modification of the zeolite using such solution. Typically, water is used as the solvent. The zeolite may be modified by only mixing it with the calcium-containing compound and phosphorus-containing compound in the form of solid or slurry (mixing process). In the mixing process, crystalline calcium phosphate (for example, $CaHPO_4.2H_2O$) crystallized from such modifying solution as used in the above-described impregnation process and fractionated from the mother liquor may be used as a solid material for modifying. Alternatively, crystalline calcium phosphate such as $CaHPO_4.2H_2O$, $CaHPO_4$, $Ca_2P_2O_7$ or the like which is commercially available may be used as the modifying solid material. The mixing with the zeolite may be carried out using the zeolite and modifying material in the form of solid. Also, it may be carried out in the form of slurry obtained by dispersing the solid zeolite and modifying material in a dispersion medium. In the present invention, the incorporation of the calcium-containing compound and phosphorus-containing compound in the zeolite is particularly conveniently carried out by impregnating the zeolite with solution containing both the compounds to carry crystalline calcium phosphate on the zeolite or mixing powder of solid-like calcium phosphate (for example, $CaHPO_4.2H_2O$) with the zeolite. The zeolite modified by such calcium phosphate exhibits highly improved catalytic performance.

The contents of the calcium-containing compound and phosphorus-containing compound in the zeolite are generally at least 0.7 wt.% based on calcium and at least 0.7 wt.% based on phosphorus, respectively, and preferably at least 1.0 wt.% and at least 1.0 wt.%, respectively. Further, it is convenient that the ratio of content between the calcium-containing compound and the phosphorus-containing compound in the zeolite is between 0.3-1.7 based on Ca/P molar ratio. The zeolite catalyst having the calcium-containing compound and phosphorus-containing compound contained therein may be used for a reaction without being subjected to any further treatment or after the calcination in an air or $N_2$ stream. Further, it may be used in a manner mixed with any suitable carrier such as, for example, clay, kaolin, alumina or the like, as desired.

The following description will be made in connection with a process for preparing lower olefin from methanol and/or dimethyl ether using the catalyst prepared as described above.

The conversion of methanol and/or dimethyl ether into lower olefin may be carried out by any reaction as long as the starting materials are supplied as gas and fully contacted with the catalyst in the form of solid. For example, it may be accomplished utilizing a fixed bed reaction system, a fluidized bed reaction system, a moving bed reaction system or the like.

The conditions for the reaction may be widely varied. For example, the reaction temperature may be selected between 300° C. and 700° C., and the weight hourly space velocity may be determined between 0.1 hr$^{-1}$ and 20 hr$^{-1}$ and preferably between 1 hr$^{-1}$ and 10 hr$^{-1}$. Overall pressure may be varied from 0.1-100 normal atmosphere and preferably from 0.5-10 normal atmosphere. Further, the starting materials may be fed onto the catalyst in a manner to be diluted by water vapor or inert gas such as nitrogen, argon or the like.

In the process of the present invention, a stream of product contains water vapor, hydrocarbon and an unreacted starting material. Suitable setting of the reaction conditions allows the proportion of lower olefin such as ethylene, propylene and the like in the hydrocarbon to be increased. The hydrocarbon product may be separated from the water vapor and purified according to any conventional procedure known in the art.

In the preparation of lower olefin in the present invention, both methanol and dimethyl ether are starting materials. Accordingly, dimethyl ether produced from methanol during the preparation may be deemed to be an unreacted material in the calculation of olefin selectivity of the catalyst.

The process for preparing lower olefin according to the present invention substantially reduces the decomposition of methanol and/or dimethyl ether into CO and $CO_2$ and allows lower olefin to be produced with high selectivity while substantially decreasing the by-production of paraffin, an aromatic compound and the like. Further, the present invention exhibits a further advantage of preventing the deposition of carbon on the catalyst, a decrease in activity of the catalyst at a high temperature and the deterioration of the catalyst.

Now, the present invention will be further described hereinafter by way of examples, and reference tests and comparison tests which were carried out in relation to the present invention. However, the present invention is not limited by the Examples, Reference Examples and Comparative Examples.

REFERENCE EXAMPLE 1

Commercially available silica sol was used as a $SiO_2$ which consists of 30 wt.% of $SiO_2$ and 70 wt.% of $H_2O$ and is manufactured and sold under a trade name of Cataloid SI-30 by Shokubai Kasei K.K. in Japan. Also, commercially available guaranteed reagents $Al(NO_3)_3.9H_2O$, NaOH and tetra-n-propyl ammonium (TPA) were used as an $Al_2O_3$ source, an alkali source and an organic crystallization agent, respectively. 80 g of silica sol was charged in a conical flask which has a magnetic stirrer coated with polypropylene placed therein, and then 788 g of $H_2O$, 0.857 g of $Al(NO_3)_3.9H_2O$, aqueous solution consisting of 10.1 g of $H_2O$ and 5.152 g of NaOH, and aqueous solution consisting of 10.1 g of $H_2O$ and 5.455 g of TPA were added to the flask in order while stirring.

This resulted in a homogeneous liquid mixture which had fluidity, was white turbid with gel and had pH of 12.9 at a room temperature. The composition of the so-formed mixture represented by a molar ratio was as follows:

$SiO_2/Al_2O_3=350$
$OH^-/SiO_2=0.322$
$TPA/SiO_2=0.0513$
$H_2O/SiO_2=120$

Then, the conical flask having the mixture received therein was equipped with a reflux condenser and heated under reflux for 11 days while stirring on an oil bath equipped with a magnetic stirrer and kept at a temperature of 110° C. A product was then separated from the mother liquor by a centrifugal separator (above 3000 rpm) while repeating water washing. The product was subjected to X-ray diffraction determination (XRD) using CuKα rays to carry out the identification of phase and further subjected to analysis by means of a scanning electron microscope (SEM) to determine the crystal grain size. The XRD revealed that the resultant material or product is a typical Na-TPA-ZSM-5 type zeolite. The average crystal grain size of the product was determined to be about 3 μm by the SEM analysis.

The so-prepared ZSM-5 type zeolite catalyst was subjected to an activation treatment in order to evaluate the characteristics of the zeolite catalyst and the catalytic performance thereof in the conversion reaction of methanol. First, the Na-TPA-ZSM-5 type zeolite was calcined for 20 hours in air to carry out the thermal decomposition of TPA to obtain Na-H-ZSM-5 type zeolite, which was then subjected to an ion exchange treatment using 0.6N HCl at a temperature of 80° C. and then to a heating treatment at 500° C. for 20 hours again to obtain H-ZSM-5 type zeolite (Sample A1). The following characteristics of Sample A1 were determined.

BET Specific Surface Area:

500 mg of Sample A1 (H-ZSM-5 type zeolite) was subjected to a vacuum degassing treatment for 30 minutes at a temperature of 150° C. under pressure of $10^{-4}$ Torr and to a $N_2$ gas adsorption equilibrium test at a temperature of liquid nitrogen to determine the specific surface area of the sample.

Hexane Isomer Adsorption and Separation Characteristics:

100 mg of Sample A1 (H-ZSM-5 type zeolite) was charged in each of stainless columns of 3 mm in inner diameter and subjected to a degassing treatment in a He stream for 1 hour. Then, a mixture of three kinds of hexane isomers different in molecular diameter from one another or a mixture of 2,2-dimethyl butane (effective molecular diameter: 7.0 Å), 3-methyl pentane (5.6 Å) and n-hexane (3.1 Å) was injected in the amount of 2 μl into each column according to a pulse method. Subsequently, each of the columns was subjected to gas chromatography to analyze effluent components of the sample from the column, to thereby determine the adsorption capacity of each of the isomers in the form of pulse frequency or number. The hexane isomer adsorption capacity of Sample A1 or the 2,2-dimethyl butane/3-methyl pentane/n-hexane adsorption pulse number of the sample was 0-9-25.

Total Acid Content:

1 g of Sample A1 (H-ZSM-5 type zeolite) was subjected to a vacuum degassing treatment at a temperature of 450° C. under pressure of $10^{-4}$ Torr for 2 hours. Then, the sample was cooled to a temperature of 100° C. and $NH_3$ gas was introduced into the sample under pressure of 14–16 Torr. The sample was kept at 100° C. for one hour. Thereafter, the sample was subjected to a degassing treatment at the same temperature under pressure of $10^{-4}$ Torr for one hour and then heated to 600° C. at a heating rate of 5° C./min according to a heat-up to quantitatively determine the removal of $NH_3$ at each temperature. The difference in removal of $NH_3$ from 100° C. to 600° C. was defined to be a total acid content. The so-obtained total acid content of Sample A1 was 0.26 meq/g.

REFERENCE EXAMPLE 2

Reference Example 1 was substantially repeated except that the $H_2O/SiO_2$ charge molar ratio in a starting mixture was 10.6 and the crystallization time (heating time under reflux while stirring) was 8 days, so that a microcrystalline ZSM-5 type zeolite was prepared which was of about 0.3 μm in average crystal grain size. The zeolite was subjected to an activation treatment according to such a procedure as described in Reference Example 1 to obtain H-ZSM-5 type zeolite (Sample A2). It was found that Sample A2 has a BET specific surface area of 294.8 m$^2$/g, a hexane isomer adsorption capacity of 0-7-17, a total acid content of 0.20 meq/g, and an actually measured $SiO_2/Al_2O_3$ of 425.7.

REFERENCE EXAMPLE 3

Reference Example 2 was substantially repeated except that $SiO_2/Al_2O_3$ charge ratio and $H_2O/SiO_2$ charge ratio in a starting mixture respectively were 800 and 8, so that a microcrystalline ZSM-5 type zeolite was prepared which was about 0.3 μm in average crystal grain size. The zeolite was subjected to an activation treatment according to Reference Example 2 to obtain H-ZSM-5 type zeolite (Sample A3). The sample had a BET specific surface area of 359.4 m$^2$/g, a hexane isomer adsorption capacity of 0-9-27, a total acid content of 0.19 meq/g and an actually measured $SiO_2/Al_2O_3$ of 779.5.

REFERENCE EXAMPLE 4

5 g of Sample A1 (H-ZSM-5 type zeolite) was added to aqueous solution obtained by mixing 250 ml of 0.1M $Ca(OCOCH_3)_2$ and 250 ml of 0.1M $NH_4H_2PO_4$ on a water bath (100° C.) and immersed in the solution on the water bath for one hour to obtain an intermediate product. The product was subjected to filtration under reduced pressure and washed with 1 l of water to obtain a white solid product. Thereafter, the product was dried at a temperature of 110° C. and then calcined at 500° C. for 20 hours to prepare a ZSM-5 type zeolite catalyst modified by calcium phosphate (Sample B1).

REFERENCE EXAMPLE 5

Reference Example 4 was substantially repeated using 7 g of Sample A2 prepared in Reference Example 2, except that the concentration of each of calcium acetate and ammonium dihydrogen phosphate was determined to be 0.0125M, so that a calcium phosphate modified ZSM-5 type zeolite catalyst (Sample B2a) may be prepared. The so-prepared catalyst (Sample B2a) had a BET specific surface area of 292.5 m$^2$/g, a hexane isomer adsorption capacity of 0-7-17, and a total acid content of 0.20 meq/g. X-ray fluorescence analysis revealed that Sample B2a had a Ca content of 1.24 wt.% and a P content of 0.73 wt.%, and a Ca/P ratio was 1.32.

REFERENCE EXAMPLE 6

Reference Example 5 was substantially repeated to prepare a calcium phosphate modified ZSM-5 type zeolite catalyst (Sample B2b), except that the concentration of each of calcium phosphate and ammonium dihydrogen phosphate was determined to be 0.025M. It was found that the so-formed Sample B2b had a BET specific surface area of 274.1 m$^2$/g, a hexane isomer adsorption capacity of 0-7-17 and a total acid content of 0.20 meq/g. Further, it was determined that Ca and P contents in Sample B2b respectively were 2.70 wt.% and 1.26 wt.%.

REFERENCE EXAMPLE 7

Reference Example 5 was substantially repeated to prepare a calcium phosphate modified ZSM-5 type zeolite catalyst (Sample B2c), except that the concentration of each of calcium acetate and ammonium dihydrogen phosphate was determined to be 0.05M. The so-obtained zeolite catalyst (Sample B2c) had a BET specific surface area of 263.8 m$^2$/g, a hexane isomer adsorption capacity of 0-7-17 and a total acid content of 0.17 meq/g. The zeolite catalyst had a Ca content of 6.34 wt.% and a P content of 2.90 wt.%.

REFERENCE EXAMPLE 8

Reference Example 5 was substantially repeated to prepare a calcium phosphate modified ZSM-5 type zeolite catalyst (Sample B2d), except that the concentration of each of calcium acetate and ammonium dihydrogen phosphate was determined to be 0.1M. The so-formed zeolite catalyst (Sample B2d) had a BET specific surface area of 234.8 m$^2$/g, a hexane isomer adsorption capacity of 0-5-15 and a total acid content of 0.15 meq/g. Also, the Ca and P contents in the zeolite catalyst were 11.23 wt.% and 5.69 wt.%, respectively.

REFERENCE EXAMPLE 9

Reference Example 4 was substantially repeated using 5 g of Sample A3 to prepare a calcium phosphate modified ZSM-5 type zeolite catalyst (Sample B3a), except that the concentration of each of calcium acetate and ammonium dihydrogen phosphate was determined to be 0.1M. It was found that the so-prepared zeolite catalyst (Sample B3a) had a BET specific surface area of 246.3 m²/g, a hexane isomer adsorption capacity of 0-7-19, a total acid content of 0.14 meq/g and an actually measured $SiO_2/Al_2O_3$ molar ratio of 1031. Also, the catalyst had a Ca content of 19.42 wt.% and a P content of 14.97 wt.%, and a Ca/P molar ratio was 1.01.

REFERENCE EXAMPLE 10

Figure 2:
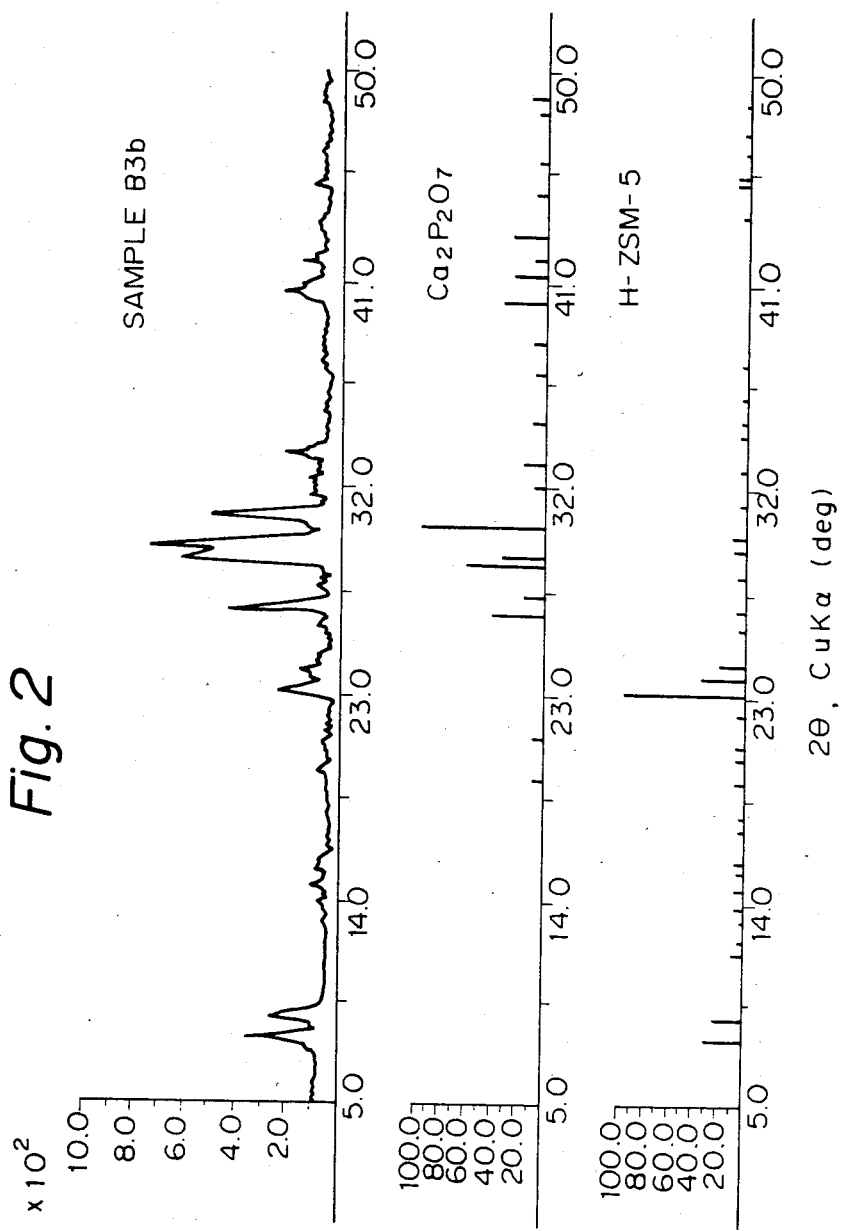
FIG. 2 is a chart showing a comparison of an X-ray diffraction pattern of a catalyst of Sample B3b (the axis of ordinates indicating diffraction intensity) with bar graphs of X-ray diffraction of $Ca_2P_2O_7$ and a standard sample H-ZSM-5 (the axis of ordinates indicating relative diffraction intensity)

Reference Example 9 was substantially repeated to prepare a calcium phosphate modified ZSM-5 type zeolite catalyst (Sample B3b), except that the concentration of each of calcium acetate and ammonium dihydrogen phosphate was determined to be 1M. The so-prepared zeolite catalyst had an X-ray diffraction pattern (use of CuKα, applied voltage and current: 40 kV and 30 mA) shown in FIG. 2, which also shows X-ray diffraction patterns of a standard sample H-ZSM-5 ($SiO_2/Al_2O_3 = 800$) and $Ca_2P_2O_7$ (JCPDS No. 17-4) defined in JCPDS for comparison. FIG. 2 clearly shows that the zeolite catalyst obtained in this reference example is a calcium phosphate modified zeolite of which a matrix is H-ZSM-5. Also, it was found that calcium phosphate contained in the catalyst mainly consists of $Ca_2P_2O_7$.

The following Comparative Examples illustrate the preparation of lower olefin which was carried out using each of H-ZSM-5 type zeolites (Sample A1, A2 and A3) and calcium phosphate modified zeolites (Samples B1, B2a–B2d, B3a and B3b) obtained in the respective reference examples described above as a catalyst.

COMPARATIVE EXAMPLE 1

The conversion reaction of methanol was carried out using Sample A1 (H-ZSM-5 type zeolite) obtained in Reference Example 1 as a catalyst in an atmospheric flow system utilizing a fixed bed. Source gas diluted by argon so as to provide methanol partial pressure of 0.5 normal atmosphere was passed through the catalyst layer at a methanol reduced LHSV (liquid hourly space velocity) of 2 hr⁻¹. The reaction was initiated at a temperature of 320° C. and the reaction temperature was raised to 340° C., 360° C., 400° C., 440° C., 500° C., 560° C. and 600° C. every two hours in turn. Products obtained at the respective reaction temperatures were subjected to gas chromatography. The results were as shown in Table 1, which indicates the methanol conversion and effective conversion in each conversion reaction and the selectivity of each component of each effectively converted product based on carbon in a temperature range between about 360° C. at which an increase in yield of lower olefin is observed and about 600° C. As is clearly indicated in Table 1, Sample A1 having a relatively large grain size of about 3 μm allowed the yield of lower olefin to be maximum at a temperature of about 560° C. and tended to somewhat cause the deterioration of the catalytic activity to decrease the yield of lower olefin when the reaction temperature exceeds 560° C. However, Sample A1 is characterized in that it exhibits a high shape-selective effect and allows the yield of ethylene to be highly increased, as compared with microcrystalline ZSM-5 type zeolite catalysts used in the following comparative examples.

The definition of several terms used herein is as follows:

Effective conversion (%):
Yield (based on carbon) of carbonaceous product except dimethyl ether in a product obtained by the conversion of methanol Selectivity (%):
Selectivity (based on carbon) of each component in an effectively converted product
C-%: % represented on the basis of carbon
C2'+C3': Total yield of ethylene+propylene
C2'−C4: Total yield of ethylene+propylene+butene
C2': Ethylene
C2: Ethane
C3: Propane
C4': Butene
i-C4: Isobutene
n-C4: n-butene
C5': pentene
C5: pentane

COMPARATIVE EXAMPLE 2

A test of a catalyst life in a methanol conversion reaction was carried out by charging 2 ml of Sample A2 (microcrystalline H-ZSM-5 type zeolite) in a silica reaction tube of 10 mm in inner diameter for a methanol conversion reaction according to an atmospheric flow system utilizing a fixed bed and carrying out the reaction under the conditions that a methanol/argon ratio was 1:1, a methanol reduced LHSV was 2 hr⁻¹ and a reaction temperature was 550° C. The results were as shown in Table 2 and FIG. 1, which indicate that the effective conversion of methanol into hydrocarbon was substantially kept at above 98 C-% over about 46 hours and the catalytic activity was rapidly deteriorated beyond 46 hours. Thus, it can be deemed that the catalyst has a life of about 46 hours. Further, the ethylene+propylene selectivity of this sample at the initial stage of the reaction (one hour after the start of the reaction) is 59.51 C-%. Thus it will be noted that the selectivity is relatively high. However, the selectivity was linearly rapidly decreased with the progress of the reaction, and the rate of change of the ethylene+propylene selectivity with time calculated by treating measuring points at which the effective conversion (hereinafter referred to as "rate of change of (C2'+C3') selectivity with time") is kept at 98 C-% or more according to a method of least square was −0.435 C-%/h which is a relatively large negative value.

COMPARATIVE EXAMPLE 3

A test of a catalyst life in a methanol conversion reaction was carried out using Sample A3 (microcrystalline H-ZSM-5 type zeolite) obtained in Reference Example 3 as a catalyst according to substantially the same procedure as in Comparative Example 2. The results were as shown in Table 3 and FIG. 1, which indicate that the catalyst had a life of about 160 hours and the rate of change of (C2'+C3') selectivity with time was −0.091 C-%/h.

The comparison of the results with those of Reference Example 2 clearly reveals that a microcrystalline H-ZSM-5 type zeolite of 0.3 μm in grain size which has a high $SiO_2/Al_2O_3$ charge molar ratio and a low $H_2O/SiO_2$ is useful as a catalyst for a methanol conversion reaction catalyst; because the higher the $SiO_2/Al_2O_3$ charge molar ratio is and the lower the $H_2O/SiO_2$ charge molar ratio is, the longer the catalytic life is and the smaller the absolute value of rate of change of (C2'+C3') selectivity with time is.

EXAMPLE 1

A methanol conversion reaction as in Comparative Example 1 was carried out using Sample B1 (calcium phosphate modified ZSM-5 type zeolite) obtained in Reference Example 4. The results were as shown in Table 4, which indicate that the modification of a H-ZSM-5 type zeolite catalyst of about 3 $\mu$m in crystal grain size with calcium phosphate substantially eliminates the deterioration of the catalyst at a high temperature and allows the yield of ethylene+propylene at a reaction temperature of 600° C. to reach a surprisingly high level of 67.63 C-%, which indicates that the yield is improved by about 20 C-%. This is becomes clearer when Table 4 is compared with Table 1 showing the results of Comparative Example 1. Further, the yield of ethylene+propylene+butene reaches as high as 76.73 C-%, and the yield of ethylene at 600° C. was as high as 27.13 C-%. Thus, it will be noted that the modification of zeolite with calcium phosphate in the present invention has an advantageous effect on the preparation of lower olefin.

EXAMPLES 2–5

A test of catalytic life of a catalyst in a methanol conversion reaction took place using each of Samples B2a–B2d (calcium phosphate modified ZSM-5 type zeolites) obtained in Reference Examples 5–8 according to a procedure as in Comparative Example 2. The results were as shown in Tables 5a–5b and FIG. 1, which indicate that the modification of an H-ZSM-5 type zeolite catalyst matrix (Sample A2) with calcium phosphate allowed the catalyst to have a life twice as long as the catalyst of Comparative Example 2 (Table 2 and FIG. 1) and the absolute value of rate of change of (C2'+C3') selectivity with time in the catalyst was remarkably decreased with the amount of calcium phosphate carried on the catalyst matrix. In particular, Sample B2d having the largest amount of calcium phosphate carried thereon had a catalytic life 4.6 times as long as the H-ZSM-5 type zeolite catalyst matrix (Sample A2) free of calcium phosphate. Further, it should be noted that the lower olefin formation capacity of the calcium phosphate modified ZSM-5 type zeolite catalyst was improved by several C-% as compared with the catalyst matrix free of calcium phosphate.

As can be seen from the foregoing, the modification of the zeolite matrix with calcium phosphate allows the catalytic life to be lengthened twice as long as the matrix and the yield of lower olefin to be highly improved, with an increase in calcium phosphate carried on the matrix.

EXAMPLE 6

A test of a catalytic life of a catalyst in a methanol conversion reaction was carried out using Sample B3a (calcium phosphate modified ZSM-5 type zeolite) obtained in Reference Example 9 according to a procedure as described in Comparative Example 3. The results were as shown in Table 6 and FIG. 1, which indicate that the modificatioin of microcrystalline ZSM-5 type zeolite catalyst matrix (Sample A3) allowed the catalytic life to extend to about 326 hours which correspond to twice or more as long as that in Comparative Example 3 (Table 3 and FIG. 1). Further, the modification permitted the yield of lower olefin to be improved by several C-% as compared with the zeolite matrix free of the phosphate. This indicates that the modification of the catalyst with calcium phosphate in the present invention has a remarkable advantage of improving the catalytic performance of the zeolite matrix.

EXAMPLE 7

Figure 3:
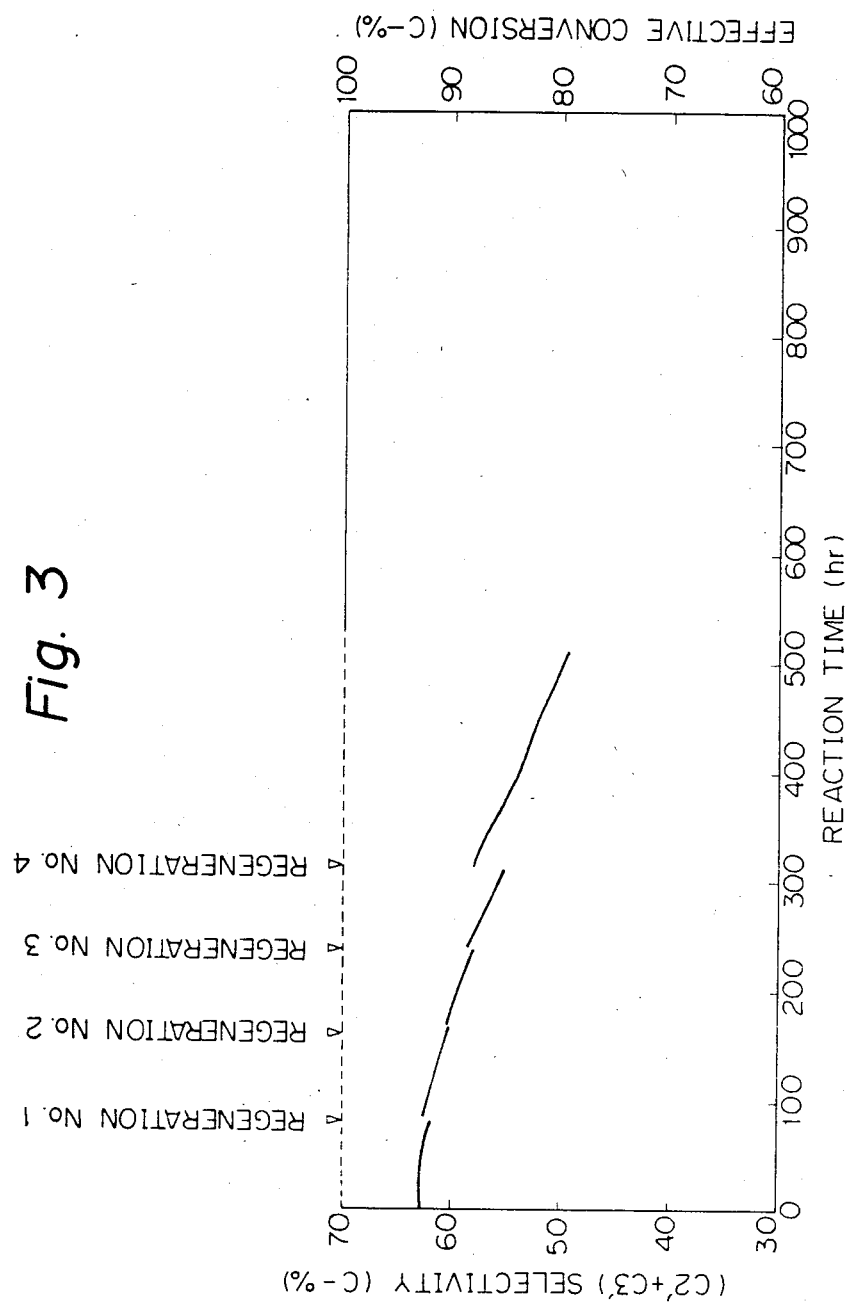
FIG. 3 is a graphical representation showing the variation of C2'+C3' selectivity and effective conversion of a catalyst with time in a methanol conversion reaction at a reaction temperature of 550° C. using Sample B3a as a catalyst.

Example 6 was substantially repeated, except that catalyst regenerating operations were carried out four times in all during the process of a methanol conversion reaction. The catalyst regeneration was carried out by introducing mixed gas of air and argon into a catalyst layer while heating the catalyst to a temperature of from 400° C. to 520° C. according to a predetermined heat-up program to regenerate the catalyst to a degree that the decomposition product gas of deposited coke such as CO, $CO_2$, $CH_4$ and the like is not observed. The results were as shown in Table 7 and FIG. 3, which indicate that although every catalyst regeneration causes the yield of lower olefin to be somewhat decreased, the effective conversion is kept substantially at 100 C-% even after the lapse of about 509 hours. Treated methanol amounted to 1018 ml/ml of catalyst or about 1467 g/g of catalyst. Further, the catalyst was highly advantageous in that the rate of change of (C2'+C3') selectivity with time at the initial state of the reaction (1–76 hours) reached −0.0077 C-%/h. Furthermore, the yield of ethylene+propylene was surprisingly kept at 60 C-% for a long period of time or for about 170 hours.

EXAMPLE 8

A methanol conversion reaction was carried out using Sample B3b obtained in Reference Example 10 according to a procedure as in Example 1. The analysis of Sample B3b by a scanning electron microscope showed that the sample mainly consisted of crystalline calcium phosphate, and ZSM-5 was dispersed on the calcium phosphate. Thus, the sample constituted a highly unique catalyst system having a zeolite matrix on which calcium phosphate was carried in large amount enough to be reasonably called "ZSM-5 modified calcium phosphate". The results were as shown in Table 8, which indicates that although calcium phosphate carried on the zeolite matrix was highly large in amount relative to the zeolite matrix, the effective conversion of methanol was kept substantially at 100% even at a high temperature of 600° C. Also, the catalyst exhibited an unexpectedly improvement on the yield of lower olefin. More particularly, the yield of ethylene+propylene and that of ethylene+propylene+butene reached 61.03 C-% and 76.10 C-%, respectively. Such a modification effect of calcium phosphate on the zeolite matrix is highly excellent and never expected from the result of Comparative Example 4 described hereinafter. Thus, it will be noted that the modification of zeolite by calcium phosphate in the present invention is essentially distinct from a conventional zeolite modification. More particularly, the fact that the carry of such a material as acting as a catalyst poison (see Table 9 showing the results of Comparative Example 4) on the zeolite matrix in large amount allows the catalytic performance to be highly improved is never expected from common knowledge obtained by catalyst chemistry.

COMPARATIVE EXAMPLE 4

A test was carried out to clarify the chemical composition of calcium phosphate and its effect on catalytic performance. Calcium phosphate was precipitated from hot solution comprising 250 ml of 0.1M $Ca(OCOCH_3)_2$ and 250 ml of 0.1M NH$_4$H$_2$PO$_4$, filtered off from the mother liquor, washed with 1 l of water, and then dried by suction to obtain a crystalline product, which was named Sample 0a.

Then, the crystalline calcium phosphate product was fully dried in an oven at a temperature of 150° C. subjected to X-ray diffraction analysis immediately thereafter to obtain a product (Sample 0b).

Further, the dried calcium phosphate was calcined at a temperature of 500° C. for 20 hours to obtain a product (Sample 0c). It was determined that Sample 0c had a BET specific surface area of 15.1 m$^2$/g, a hexane isomer adsorption capacity of 0-0-0 and a total acid content of 0.07 meq/g.

Figure 4B:
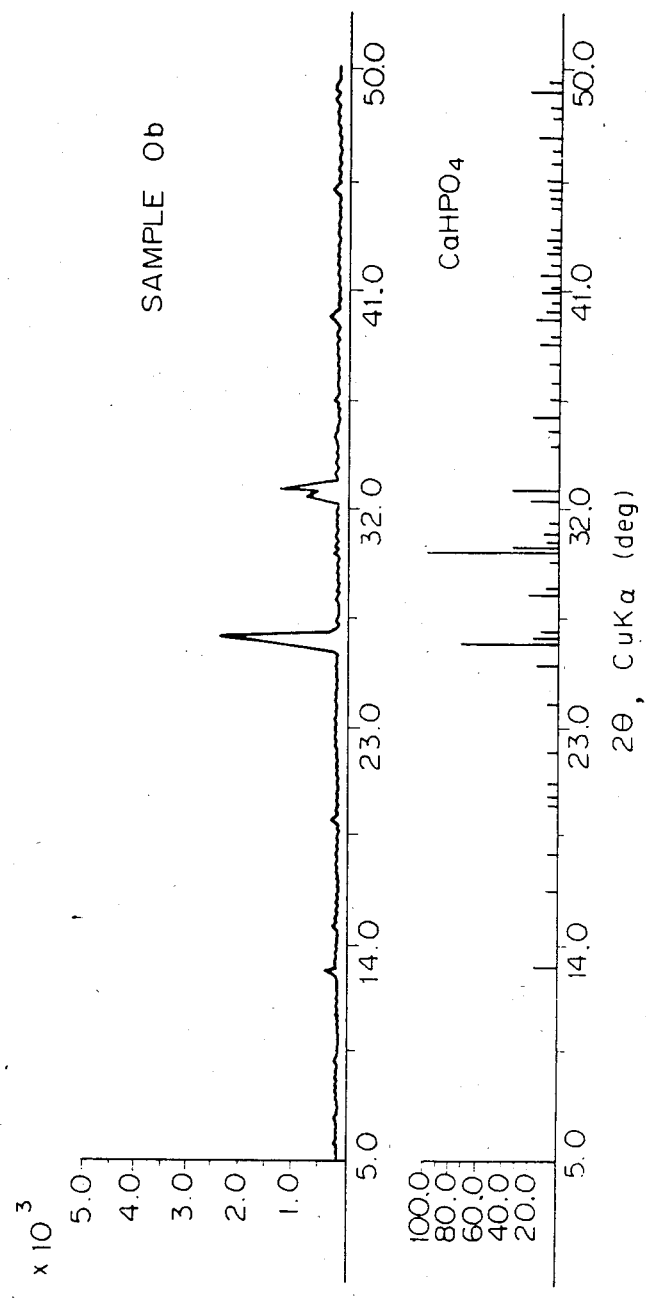
Figure 4C:
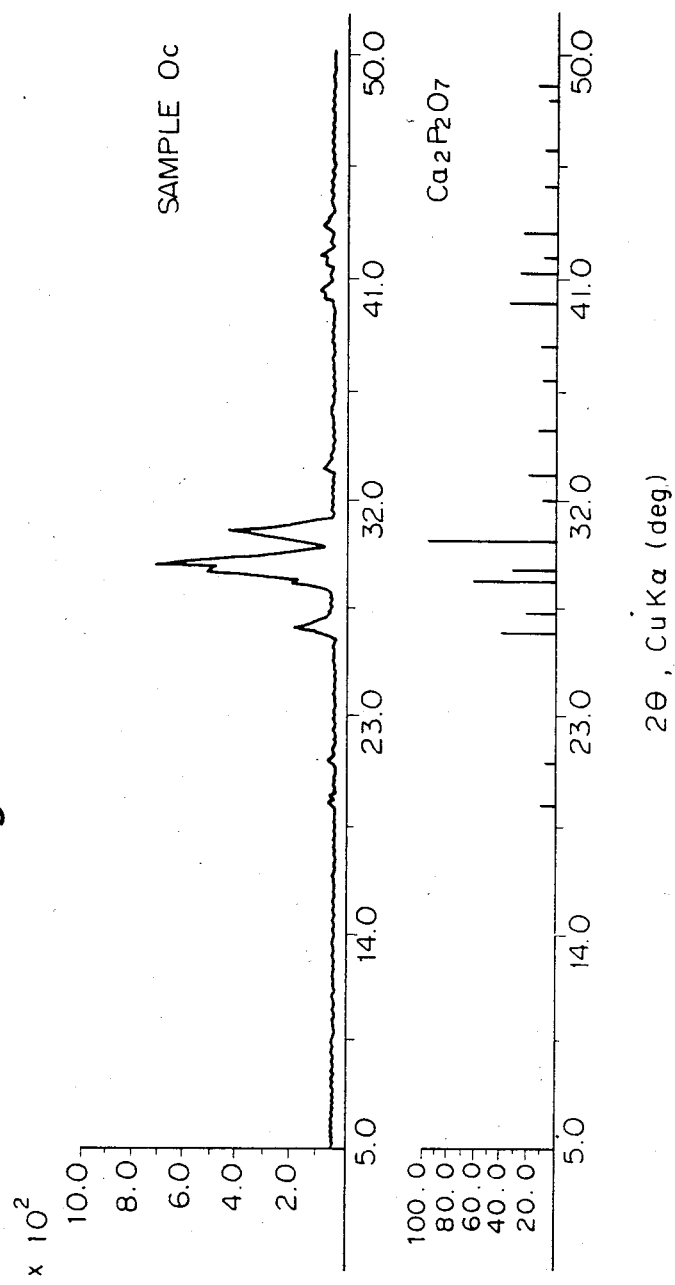

Three kinds of Samples 0a-0c or the as-made calcium phosphate, calcium phosphate dried at 110° C. and calcium phosphate calcined at 500° C., respectively, were subjected to X-ray diffraction analysis (CuKα, applied voltage and current: 50 kV and 40 mA). The results were as shown in FIGS. 4a-4c, in which X-ray diffraction patterns of JCPDS for comparison are also plotted. The comparison of the diffraction patterns of the samples with that of JCPDS indicates that Samples 0a-0c are CaHPO$_4$.2H$_2$O, CaHPO$_4$ and Ca$_2$P$_2$O$_7$, respectively. This reveals that calcium phosphate obtained during the preparation of the calcium phosphate modified ZSM-5 type zeolite catalyst used in each of the above-described examples mainly consists of at least one of CaHPO$_4$.2H$_2$O, partially dehydrated CaHPO$_4$.2H$_2$O, CaHPO$_4$, Ca$_2$P$_2$O$_7$ and derivatives thereof.

Then, a methanol conversion reaction was carried out using crystalline calcium phosphate of Sample 0c as a catalyst according to a procedure as in Example 1. The results were as shown in Table 9, which indicates that the catalyst had an activity sufficient to considerably cause the conversion of methanol into dimethyl ether over the whole reaction temperature range. However, the catalyst was considerably lower in conversion of methanol into hydrocarbon, as compared with ZSM-5. Further, in the use of Sample 0c, the hydrocarbon produced at a high temperature mainly consisted of CH$_4$, and a large amount of CO was concurrently produced. Such fact clearly indicates that the decomposition reaction of methanol is effectively highly carried out and calcium phosphate itself usually acts as a catalyst poison in a methanol conversion reaction for synthesizing lower olefin.

TABLE 1

Effect of Sample A1 on Methanol Conversion Reaction

| Reaction Time (h) | | 5 | 7 | 9 | 11 | 13 | 15 | 17 |
|---|---|---|---|---|---|---|---|---|
| Reaction Temp. (°C.) | | 361 | 401 | 441 | 500 | 539 | 559 | 599 |
| Methanol Conversion (%) | | 99.10 | 99.32 | 99.33 | 100.00 | 100.00 | 100.00 | 99.92 |
| Effective Conversion (C-%) | | 99.02 | 99.28 | 99.22 | 99.89 | 99.90 | 99.88 | 99.85 |
| Selectivity (%) | CO | 0.00 | 0.00 | 0.00 | 0.05 | 0.60 | 1.09 | 2.02 |
| | CO$_2$ | 0.00 | 0.00 | 0.00 | 0.00 | 0.00 | 0.00 | 0.20 |
| | CH$_4$ | 0.22 | 0.20 | 0.33 | 0.96 | 2.18 | 3.38 | 6.85 |
| | C2' | 6.69 | 5.78 | 8.38 | 14.14 | 17.44 | 17.01 | 15.96 |
| | C2 | 0.00 | 0.00 | 0.00 | 0.00 | 0.00 | 0.00 | 0.79 |
| | C3' | 9.30 | 15.91 | 22.39 | 27.42 | 29.46 | 31.10 | 30.62 |
| | C3 | 3.07 | 3.27 | 3.56 | 3.71 | 2.99 | 2.30 | 1.45 |
| | C4' | 10.56 | 13.64 | 14.51 | 11.36 | 9.08 | 8.55 | 7.21 |
| | i-C4 | 7.89 | 7.58 | 6.55 | 5.71 | 5.36 | 4.97 | 2.67 |
| | n-C4 | 1.66 | 1.71 | 1.66 | 1.39 | 1.02 | 0.83 | 0.53 |
| | C5' | 11.75 | 9.63 | 7.45 | 4.57 | 3.05 | 2.43 | 0.46 |
| | C5 | 7.65 | 6.85 | 6.10 | 5.22 | 4.47 | 4.21 | 2.71 |
| | Ethanol | 1.74 | 1.29 | 1.16 | 0.39 | 0.11 | 0.09 | 0.04 |
| | Benzene | 0.69 | 0.66 | 0.65 | 1.14 | 1.57 | 1.78 | 2.38 |
| | Toluene | 2.13 | 2.73 | 3.01 | 4.18 | 5.40 | 6.07 | 7.82 |
| | Xylene | 8.10 | 6.94 | 6.50 | 7.64 | 8.41 | 9.10 | 9.82 |
| | Balance | 28.54 | 23.83 | 17.75 | 12.10 | 8.86 | 7.11 | 8.46 |
| (C2' + C3') Yield (C-%) | | 15.83 | 21.53 | 30.53 | 41.51 | 46.85 | 48.05 | 46.51 |
| (C2'~C4') Yield (C-%) | | 26.29 | 35.08 | 44.93 | 52.86 | 55.92 | 56.59 | 53.71 |

TABLE 2

Effect of Sample A2 on Methanol Conversion Reaction at 550° C.

| Reaction Time (h) | | 1.0 | 21.0 | 33.5 | 41.5 | 45.5 | 47.5 | 51.5 |
|---|---|---|---|---|---|---|---|---|
| Methanol Conversion (%) | | 100.00 | 100.00 | 100.00 | 100.00 | 98.67 | 97.38 | 92.05 |
| Effective Conversion (C-%) | | 100.00 | 100.00 | 100.00 | 100.00 | 98.03 | 95.71 | 83.73 |
| Selectivity (%) | CO | 0.08 | 0.16 | 0.20 | 0.29 | 0.42 | 0.65 | 1.64 |
| | CO$_2$ | 0.00 | 0.00 | 0.00 | 0.00 | 0.00 | 0.00 | 0.05 |
| | CH$_4$ | 1.51 | 2.26 | 2.59 | 3.22 | 3.69 | 4.04 | 5.32 |
| | C2' | 14.73 | 9.93 | 7.40 | 6.61 | 6.07 | 5.72 | 4.99 |
| | C2 | 0.20 | 0.19 | 0.15 | 0.16 | 0.18 | 0.19 | 0.25 |
| | C3' | 44.78 | 43.67 | 40.99 | 36.57 | 33.27 | 30.46 | 25.31 |
| | C3 | 0.13 | 0.00 | 0.00 | 0.00 | 0.00 | 0.00 | 0.00 |
| | C4' | 14.94 | 15.44 | 14.37 | 13.07 | 11.93 | 8.67 | 7.68 |
| | i-C4 | 1.30 | 0.74 | 0.85 | 0.82 | 0.00 | 0.39 | 0.00 |
| | n-C4 | 0.63 | 0.13 | 0.12 | 0.00 | 0.05 | 0.07 | 0.06 |
| | C5' | 0.29 | 2.07 | 2.80 | 3.17 | 3.32 | 3.63 | 0.92 |

TABLE 2-continued

Effect of Sample A2 on Methanol Conversion Reaction at 550° C.

| | | | | | | | | |
|---|---|---|---|---|---|---|---|---|
| C5 | 2.87 | 3.01 | 2.82 | 2.79 | 2.65 | 2.58 | 2.47 |
| Balance | 18.54 | 22.40 | 27.72 | 33.29 | 38.41 | 43.59 | 51.32 |
| (C2' + C3') Yield (C-%) | 59.51 | 53.60 | 48.39 | 43.18 | 38.57 | 34.63 | 25.37 |
| (C2'~C4') Yield (C-%) | 74.45 | 69.04 | 62.76 | 56.25 | 50.26 | 42.93 | 31.80 |

TABLE 3

Effect of Sample A3 on Methanol Conversion Reaction at 550° C.

| Reaction Time (h) | | 1 | 21 | 61 | 99 | 165 | 190 | 219 |
|---|---|---|---|---|---|---|---|---|
| Methanol Conversion (%) | | 100.00 | 100.00 | 100.00 | 100.00 | 98.65 | 96.79 | 74.61 |
| Effective Conversion (C-%) | | 100.00 | 100.00 | 100.00 | 100.00 | 96.85 | 92.64 | 39.05 |
| Selectivity (%) | CO | 0.03 | 0.03 | 0.05 | 0.04 | 0.04 | 0.04 | 0.40 |
| | CO2 | 0.00 | 0.00 | 0.00 | 0.00 | 0.00 | 0.00 | 0.00 |
| | CH4 | 0.75 | 0.98 | 1.22 | 1.20 | 1.20 | 1.39 | 4.33 |
| | C2' | 16.37 | 12.61 | 9.68 | 7.27 | 5.64 | 4.57 | 3.00 |
| | C2 | 0.28 | 0.22 | 0.17 | 0.14 | 0.11 | 0.11 | 0.20 |
| | C3' | 42.91 | 46.76 | 47.26 | 44.40 | 39.90 | 36.69 | 22.75 |
| | C3 | 0.67 | 0.00 | 0.00 | 0.00 | 0.00 | 0.00 | 0.00 |
| | C4' | 13.69 | 15.83 | 13.47 | 12.87 | 12.07 | 13.69 | 10.60 |
| | i-C4 | 2.50 | 1.03 | 0.00 | 0.00 | 0.53 | 0.00 | 0.00 |
| | n-C4 | 0.81 | 0.33 | 0.21 | 0.17 | 0.09 | 0.09 | 0.00 |
| | C5' | 0.39 | 0.27 | 0.70 | 2.77 | 3.62 | 3.55 | 0.47 |
| | C5 | 3.14 | 2.90 | 2.98 | 2.95 | 2.95 | 2.97 | 2.43 |
| | Balance | 18.46 | 19.04 | 24.28 | 28.19 | 33.85 | 36.91 | 55.81 |
| (C2' + C3') Yield (C-%) | | 59.28 | 59.37 | 56.94 | 53.18 | 44.11 | 38.22 | 10.06 |
| (C2'~C4') Yield (C-%) | | 72.97 | 75.20 | 70.41 | 64.54 | 55.80 | 50.91 | 14.19 |

TABLE 4

Effect of Sample B1 on Methanol Conversion Reaction

| Reaction Time (h) | | 5 | 7 | 9 | 11 | 13 | 15 | 17 |
|---|---|---|---|---|---|---|---|---|
| Reaction Temp. (°C.) | | 360 | 400 | 440 | 500 | 540 | 560 | 600 |
| Methanol Conversion (%) | | 100.00 | 100.00 | 100.00 | 100.00 | 100.00 | 100.00 | 99.81 |
| Effective Conversion (C-%) | | 100.00 | 100.00 | 100.00 | 100.00 | 100.00 | 100.00 | 99.81 |
| Selectivity (%) | CO | 0.00 | 0.00 | 0.00 | 0.01 | 0.03 | 0.04 | 0.08 |
| | CO2 | 0.00 | 0.00 | 0.00 | 0.00 | 0.00 | 0.00 | 0.00 |
| | CH4 | 0.19 | 0.16 | 0.18 | 0.33 | 0.56 | 0.76 | 1.44 |
| | C2' | 6.68 | 5.67 | 8.13 | 14.91 | 20.51 | 22.93 | 27.13 |
| | C2 | 0.07 | 0.07 | 0.11 | 0.21 | 0.34 | 0.41 | 0.61 |
| | C3' | 9.83 | 16.93 | 24.69 | 35.40 | 40.03 | 40.40 | 40.63 |
| | C3 | 2.61 | 2.98 | 3.31 | 3.07 | 2.74 | 2.40 | 1.89 |
| | C4' | 9.86 | 12.27 | 14.69 | 14.05 | 12.33 | 11.03 | 9.12 |
| | i-C4 | 7.22 | 7.06 | 5.39 | 2.69 | 1.73 | 1.43 | 0.77 |
| | n-C4 | 1.53 | 1.64 | 1.63 | 1.21 | 0.93 | 0.89 | 0.59 |
| | C5' | 3.62 | 1.71 | 1.58 | 1.03 | 0.47 | 0.15 | 0.00 |
| | C5 | 8.88 | 8.23 | 6.94 | 4.98 | 3.80 | 3.44 | 2.52 |
| | Ethanol | 0.00 | 0.22 | 0.00 | 0.00 | 0.00 | 0.00 | 0.00 |
| | Benzene | 0.00 | 0.00 | 0.00 | 0.00 | 0.00 | 0.00 | 0.00 |
| | Toluene | 1.63 | 1.88 | 2.53 | 1.59 | 1.92 | 2.30 | 2.93 |
| | Xylene | 6.11 | 4.80 | 10.75 | 2.34 | 1.86 | 2.06 | 2.08 |
| | Balance | 41.77 | 36.36 | 20.08 | 18.15 | 12.74 | 11.73 | 10.20 |
| (C2' + C3') Yield (C-%) | | 16.51 | 22.60 | 32.82 | 50.31 | 60.54 | 63.33 | 67.63 |
| (C2'~C4') Yield (C-%) | | 26.37 | 34.87 | 47.51 | 64.36 | 72.87 | 74.36 | 76.73 |

TABLE 5

| | Effect of Sample B2a on Methanol Conversion Reaction at 550° C. | | | | | | | Effect of Sample B2b on Methanol Conversion Reaction at 550° C. | | | | | |
|---|---|---|---|---|---|---|---|---|---|---|---|---|---|
| Reaction Time (h) | 1.0 | 11.0 | 51.0 | 95.1 | 117.0 | 119.0 | 123.0 | 1.0 | 9.0 | 69.0 | 107.0 | 181.7 | 183.7 | 193.8 |
| Methanol Conversion (%) | 100.00 | 100.00 | 100.00 | 100.00 | 99.06 | 98.97 | 97.67 | 100.00 | 100.00 | 100.00 | 100.00 | 98.95 | 97.54 | 94.26 |
| Effective Conversion | 100.00 | 100.00 | 100.00 | 100.00 | 98.04 | 97.70 | 95.25 | 100.00 | 100.00 | 100.00 | 100.00 | 98.01 | 95.37 | 88.62 |

TABLE 5-continued

| | | | | | | | | | | | | | | | |
|---|---|---|---|---|---|---|---|---|---|---|---|---|---|---|---|
| version (C-%) | | | | | | | | | | | | | | | |
| Select- | CO | 0.00 | 0.00 | 0.00 | 0.00 | 0.00 | 0.00 | 0.00 | 0.00 | 0.00 | 0.00 | 0.00 | 0.00 | 0.00 | 0.00 |
| tivity | $CO_2$ | 0.00 | 0.00 | 0.00 | 0.00 | 0.00 | 0.00 | 0.00 | 0.00 | 0.00 | 0.00 | 0.00 | 0.00 | 0.00 | 0.00 |
| (%) | $CH_4$ | 1.15 | 1.54 | 1.84 | 2.09 | 2.47 | 2.30 | 2.52 | 0.79 | 1.20 | 1.84 | 2.01 | 2.91 | 3.20 | 3.53 |
| | C2' | 18.63 | 16.43 | 11.12 | 8.00 | 6.17 | 5.99 | 5.69 | 20.23 | 19.75 | 13.99 | 11.12 | 5.53 | 5.11 | 4.46 |
| | C2 | 0.00 | 0.00 | 0.00 | 0.17 | 0.00 | 0.18 | 0.15 | 0.22 | 0.00 | 0.00 | 0.28 | 0.00 | 0.18 | 0.19 | 0.23 |
| | C3' | 39.81 | 43.03 | 44.40 | 41.59 | 36.11 | 35.30 | 33.99 | 40.98 | 44.01 | 46.22 | 45.14 | 35.97 | 34.23 | 30.63 |
| | C3 | 1.68 | 1.25 | 0.69 | 0.43 | 0.32 | 0.31 | 0.30 | 1.72 | 1.51 | 0.79 | 0.57 | 0.25 | 0.25 | 0.21 |
| | C4' | 12.37 | 14.01 | 15.57 | 14.56 | 13.22 | 13.02 | 12.77 | 12.23 | 13.36 | 15.13 | 15.31 | 13.10 | 12.98 | 12.35 |
| | i-C4 | 2.03 | 1.50 | 0.90 | 0.70 | 0.53 | 0.53 | 0.50 | 1.61 | 1.29 | 0.74 | 0.66 | 0.43 | 0.43 | 0.37 |
| | n-C4 | 0.59 | 0.46 | 0.30 | 0.21 | 0.16 | 0.15 | 0.15 | 0.60 | 0.49 | 0.31 | 0.26 | 0.14 | 0.14 | 0.12 |
| | C5' | 0.11 | 3.87 | 6.93 | 10.58 | 8.89 | 8.84 | 6.02 | 0.09 | 3.25 | 4.31 | 6.52 | 13.10 | 13.44 | 13.19 |
| | C5 | 4.54 | 4.36 | 4.62 | 4.56 | 4.64 | 4.61 | 4.60 | 4.16 | 4.05 | 4.35 | 4.74 | 4.36 | 4.39 | 4.21 |
| | Balance | 19.08 | 13.56 | 13.46 | 17.28 | 27.32 | 28.81 | 33.24 | 17.60 | 11.09 | 12.05 | 13.67 | 24.02 | 25.64 | 30.70 |
| (C2' + C3') Yield (C-%) | | 58.44 | 59.46 | 55.52 | 49.59 | 41.45 | 40.34 | 37.80 | 61.21 | 63.76 | 60.21 | 56.26 | 40.67 | 37.52 | 31.10 |
| (C2'~C4') Yield (C-%) | | 70.81 | 73.47 | 71.09 | 64.15 | 54.41 | 53.06 | 49.96 | 73.44 | 77.12 | 75.34 | 71.57 | 53.51 | 49.90 | 42.04 |

| | Effect of Sample B2a on Methanol Conversion Reaction at 550° C. | | | | | | | Effect of Sample B2b on Methanol Conversion Reaction at 550° C. | | | | | | |
|---|---|---|---|---|---|---|---|---|---|---|---|---|---|---|
| Reaction Time (h) | 1.0 | 26.0 | 109.0 | 135.0 | 155.2 | 161.2 | 171.2 | 1.0 | 11.5 | 135.5 | 185.7 | 211.5 | 225.5 | 241.5 |
| Methanol Conversion (%) | 100.00 | 100.00 | 100.0 | 100.0 | 99.20 | 94.68 | 82.92 | 100.00 | 100.00 | 100.00 | 100.00 | 99.21 | 95.83 | 88.18 |
| Effective Conversion (C-%) | 100.00 | 100.00 | 100.00 | 100.00 | 98.03 | 89.03 | 56.51 | 100.00 | 100.00 | 100.00 | 100.00 | 98.30 | 91.99 | 74.74 |
| Selec- CO | 0.00 | 0.00 | 0.00 | 0.00 | 0.00 | 0.00 | 0.00 | 0.00 | 0.00 | 0.00 | 0.00 | 0.00 | 0.00 | 0.00 |
| tivity $CO_2$ | 0.00 | 0.00 | 0.00 | 0.00 | 0.00 | 0.00 | 0.00 | 0.00 | 0.00 | 0.00 | 0.00 | 0.00 | 0.00 | 0.00 |
| (%) $CH_4$ | 0.76 | 1.34 | 1.25 | 1.18 | 1.56 | 2.17 | 3.54 | 0.73 | 0.85 | 1.36 | 1.62 | 1.93 | 1.89 | 2.66 |
| C2' | 19.27 | 16.63 | 12.28 | 10.46 | 7.82 | 7.01 | 5.87 | 18.09 | 16.88 | 11.01 | 8.37 | 6.49 | 5.14 | 3.82 |
| C2 | 0.00 | 0.00 | 0.00 | 0.00 | 0.15 | 0.15 | 0.23 | 0.00 | 0.00 | 0.00 | 0.00 | 0.00 | 0.09 | 0.14 |
| C3' | 43.84 | 43.56 | 44.58 | 44.33 | 37.60 | 34.05 | 28.50 | 44.52 | 43.65 | 43.71 | 41.39 | 36.98 | 33.06 | 28.70 |
| C3 | 1.34 | 1.09 | 0.74 | 0.55 | 0.36 | 0.30 | 0.23 | 1.21 | 1.12 | 0.62 | 0.43 | 0.31 | 0.25 | 0.19 |
| C4' | 13.92 | 14.42 | 15.89 | 15.48 | 13.35 | 12.68 | 11.48 | 14.84 | 14.59 | 15.39 | 14.37 | 13.44 | 12.83 | 12.11 |
| i-C4 | 0.98 | 0.82 | 0.77 | 0.71 | 0.52 | 0.46 | 0.38 | 0.89 | 0.85 | 0.69 | 0.58 | 0.49 | 0.44 | 0.37 |
| n-C4 | 0.45 | 0.39 | 0.32 | 0.27 | 0.20 | 0.16 | 0.12 | 0.45 | 0.41 | 0.27 | 0.20 | 0.17 | 0.16 | 0.11 |
| C5' | 2.14 | 2.36 | 3.82 | 7.21 | 8.97 | 9.14 | 8.62 | 2.54 | 2.54 | 6.62 | 9.18 | 9.92 | 9.97 | 9.78 |
| C5 | 4.11 | 4.17 | 4.61 | 4.65 | 4.57 | 4.53 | 4.00 | 4.30 | 4.23 | 4.54 | 4.61 | 4.70 | 4.69 | 4.27 |
| Balance | 13.20 | 15.21 | 15.73 | 15.16 | 24.88 | 29.34 | 37.04 | 12.44 | 14.89 | 15.78 | 19.25 | 25.57 | 31.47 | 37.84 |
| (C2' + C3') Yield (C-%) | 63.11 | 60.19 | 56.86 | 54.79 | 44.53 | 36.56 | 19.42 | 62.61 | 60.51 | 54.72 | 49.76 | 42.73 | 35.14 | 24.31 |
| (C2'~C4') Yield (C-%) | 77.03 | 74.61 | 72.75 | 70.27 | 57.61 | 47.84 | 25.91 | 77.45 | 75.10 | 70.11 | 64.13 | 55.94 | 46.94 | 33.36 |

TABLE 6

Effect of Sample B3a on Methanol Conversion Reaction at 550° C.

| | 1 | 59 | 155 | 251 | 325 | 327 | 339 |
|---|---|---|---|---|---|---|---|
| Reaction Time (h) | | | | | | | |
| Methanol Conversion (%) | 99.42 | 99.34 | 99.20 | 99.09 | 98.35 | 96.20 | 95.20 |
| Effective Conversion (C-%) | 99.42 | 99.34 | 99.20 | 99.05 | 98.35 | 96.04 | 95.20 |
| Selec- CO | 0.00 | 0.03 | 0.04 | 0.00 | 0.06 | 0.00 | 0.00 |
| tivity $CO_2$ | 0.00 | 0.00 | 0.00 | 0.00 | 0.00 | 0.00 | 0.00 |
| (%) $CH_4$ | 0.55 | 0.78 | 0.78 | 0.85 | 0.67 | 0.79 | 0.92 |
| C2' | 16.68 | 14.02 | 10.76 | 7.82 | 5.49 | 5.65 | 5.25 |
| C2 | 0.00 | 0.00 | 0.00 | 0.00 | 0.09 | 0.00 | 0.00 |
| C3' | 46.74 | 46.09 | 46.15 | 46.01 | 39.52 | 39.97 | 38.41 |
| C3 | 1.09 | 0.78 | 0.56 | 0.42 | 0.31 | 0.30 | 0.29 |
| C4' | 16.58 | 16.79 | 17.41 | 17.46 | 15.53 | 15.75 | 15.38 |
| i-C4 | 0.70 | 0.57 | 0.53 | 0.54 | 0.46 | 0.46 | 0.44 |
| n-C4 | 0.37 | 0.29 | 0.24 | 0.20 | 0.16 | 0.16 | 0.16 |
| C5' | 3.60 | 4.18 | 7.72 | 11.69 | 13.30 | 13.50 | 13.57 |
| C5 | 4.48 | 4.55 | 4.75 | 5.15 | 4.98 | 5.18 | 5.14 |
| Balance | 9.22 | 11.93 | 11.76 | 9.87 | 19.48 | 18.24 | 20.44 |
| (C2' + C3') Yield (C-%) | 63.05 | 59.71 | 56.45 | 53.32 | 44.27 | 43.81 | 41.57 |
| (C2'~C4') Yield (C-%) | 79.54 | 76.39 | 73.73 | 70.61 | 59.54 | 58.94 | 56.22 |

TABLE 7

Effect of Sample B3a and Its Regenerations on Methanol Conversion Reaction at 550° C.

| | | | | | | First Regeneration | | | | Second Regeneration | | | |
|---|---|---|---|---|---|---|---|---|---|---|---|---|---|
| Reaction Time (h) | 1.0 | 21.4 | 61.9 | 75.9 | 77.9 | 86.3 | 121.7 | 156.7 | 158.7 | 170.2 | 199.8 | 215.7 | 233.7 |
| Methanol Conversion (%) | 99.39 | 99.36 | 99.32 | 99.30 | 99.33 | 99.29 | 99.26 | 99.20 | 99.23 | 99.22 | 98.82 | 99.11 | 99.10 |
| Effective Conversion (C-%) | 99.39 | 99.36 | 99.32 | 99.30 | 98.03 | 99.23 | 99.26 | 99.20 | 99.23 | 99.15 | 98.82 | 99.11 | 99.10 |
| Selec- CO | 0.40 | 0.00 | 0.27 | 0.00 | 0.00 | 0.00 | 0.05 | 0.00 | 0.09 | 0.00 | 1.18 | 0.00 | 0.00 |
| tivity $CO_2$ | 0.00 | 0.00 | 0.00 | 0.00 | 0.00 | 0.00 | 0.00 | 0.00 | 0.00 | 0.00 | 0.00 | 0.00 | 0.00 |
| (%) $CH_4$ | 0.38 | 0.56 | 0.65 | 0.77 | 0.59 | 5.29 | 0.84 | 0.90 | 0.25 | 0.74 | 3.29 | 0.97 | 1.05 |
| C2' | 16.14 | 15.43 | 14.22 | 13.80 | 14.27 | 14.10 | 12.56 | 11.89 | 12.78 | 12.47 | 11.76 | 10.82 | 10.26 |
| C2 | 0.00 | 0.00 | 0.00 | 0.00 | 0.00 | 0.00 | 0.00 | 0.00 | 0.06 | 0.07 | 0.00 | 0.00 | 0.00 |
| C3' | 46.49 | 47.05 | 47.98 | 47.97 | 47.69 | 48.47 | 47.71 | 48.36 | 46.66 | 47.56 | 48.62 | 46.94 | 46.81 |
| C3 | 0.98 | 0.94 | 0.82 | 0.79 | 0.85 | 0.83 | 0.73 | 0.65 | 0.72 | 0.67 | 0.61 | 0.55 | 0.53 |
| C4' | 16.83 | 17.18 | 17.78 | 17.88 | 17.49 | 17.84 | 17.83 | 18.21 | 17.31 | 17.74 | 18.31 | 17.78 | 17.80 |
| i-C4 | 0.65 | 0.65 | 0.64 | 0.62 | 0.63 | 0.64 | 0.62 | 0.59 | 0.59 | 0.60 | 0.56 | 0.54 | 0.52 |

TABLE 7-continued

Effect of Sample B3a and Its Regenerations on Methanol Conversion Reaction at 550° C.

|  | | | | | | | | | | | | | |
|---|---|---|---|---|---|---|---|---|---|---|---|---|---|
| n-C4 | 0.35 | 0.34 | 0.30 | 0.32 | 0.32 | 0.32 | 0.29 | 0.29 | 0.28 | 0.27 | 0.00 | 0.23 | 0.22 |
| C5' | 3.78 | 4.49 | 5.11 | 4.78 | 4.08 | 4.93 | 5.62 | 6.47 | 4.37 | 5.52 | 5.61 | 6.18 | 7.52 |
| C5 | 4.58 | 4.68 | 4.76 | 4.90 | 4.78 | 4.89 | 4.88 | 4.97 | 4.73 | 4.83 | 4.88 | 4.82 | 4.82 |
| Balance | 9.43 | 8.69 | 7.17 | 8.16 | 9.31 | 10.78 | 8.76 | 7.68 | 12.76 | 9.52 | 5.15 | 11.18 | 10.47 |
| (C2' + C3') Yield (C-%) | 62.25 | 62.08 | 62.07 | 61.35 | 61.54 | 62.09 | 59.82 | 59.77 | 58.98 | 59.52 | 59.67 | 57.25 | 56.56 |
| (C2'~C4') Yield (C-%) | 78.98 | 79.15 | 79.72 | 79.10 | 78.92 | 79.79 | 77.52 | 77.83 | 76.16 | 77.11 | 77.75 | 74.87 | 74.20 |

| | Third Regeneration | | | Fourth Regeneration | | | | | | |
|---|---|---|---|---|---|---|---|---|---|---|
| Reaction Time (h) | 235.7 | 271.3 | 311.2 | 313.2 | 340.7 | 380.3 | 420.5 | 460.7 | 480.6 | 488.6 | 508.6 |
| Methanol Conversion (%) | 99.08 | 99.05 | 99.03 | 99.07 | 98.99 | 98.95 | 98.91 | 98.93 | 98.93 | 98.99 | 99.15 |
| Effective Conversion (C-%) | 99.08 | 98.90 | 99.03 | 99.07 | 98.99 | 98.95 | 98.91 | 98.93 | 98.89 | 98.99 | 99.15 |
| Selectivity (%) CO | 0.03 | 0.00 | 0.00 | 0.00 | 0.00 | 0.04 | 0.00 | 0.05 | 0.00 | 0.00 | 0.00 |
| CO2 | 0.00 | 0.00 | 0.00 | 0.00 | 0.00 | 0.00 | 0.00 | 0.00 | 0.00 | 0.00 | 0.00 |
| CH4 | 0.94 | 1.02 | 0.91 | 0.84 | 1.22 | 0.95 | 1.12 | 1.03 | 0.93 | 1.09 | 0.95 |
| C2' | 12.03 | 9.97 | 9.05 | 10.59 | 9.56 | 8.00 | 7.81 | 7.29 | 6.51 | 6.34 | 5.87 |
| C2 | 0.00 | 0.00 | 0.00 | 0.00 | 0.00 | 0.00 | 0.00 | 0.00 | 0.00 | 0.00 | 0.00 |
| C3' | 46.19 | 46.54 | 45.85 | 46.49 | 46.69 | 45.88 | 46.99 | 45.29 | 44.16 | 43.69 | 42.55 |
| C3 | 0.62 | 0.51 | 0.46 | 0.58 | 0.49 | 0.42 | 0.42 | 0.38 | 0.34 | 0.34 | 0.31 |
| C4' | 17.26 | 17.65 | 17.55 | 17.54 | 17.80 | 17.54 | 17.54 | 17.99 | 17.59 | 16.93 | 16.78 | 16.43 |
| i-C4 | 0.58 | 0.55 | 0.54 | 0.58 | 0.56 | 0.53 | 0.58 | 0.55 | 0.52 | 0.52 | 0.51 |
| n-C4 | 0.26 | 0.23 | 0.22 | 0.26 | 0.22 | 0.19 | 0.21 | 0.20 | 0.19 | 0.17 | 0.18 |
| C5' | 5.72 | 8.35 | 8.85 | 6.81 | 9.01 | 10.86 | 11.68 | 11.81 | 12.25 | 13.45 | 12.89 |
| C5 | 4.76 | 4.87 | 4.94 | 4.84 | 4.97 | 4.99 | 5.17 | 5.22 | 5.15 | 5.00 | 5.16 |
| Balance | 11.61 | 10.31 | 11.61 | 11.48 | 9.50 | 10.58 | 8.03 | 10.56 | 13.01 | 12.63 | 15.18 |
| (C2' + C3') Yield (C-%) | 57.68 | 55.89 | 54.37 | 56.53 | 55.68 | 53.31 | 54.20 | 52.02 | 50.11 | 49.52 | 48.01 |
| (C2'~C4') Yield (C-%) | 74.79 | 73.34 | 71.15 | 73.90 | 73.30 | 70.67 | 72.00 | 69.42 | 66.85 | 66.14 | 64.30 |

TABLE 8

Effect of Sample B3b on Methanol Conversion Reaction

| | | | | | | | |
|---|---|---|---|---|---|---|---|
| Reaction Time (h) | 5 | 7 | 9 | 11 | 13 | 15 | 17 |
| Reaction Temp. (°C.) | 360 | 400 | 440 | 499 | 540 | 560 | 599 |
| Methanol Conversion (%) | 83.26 | 95.41 | 100.00 | 100.00 | 100.00 | 99.69 | 99.94 |
| Effective Conversion (C-%) | 5.09 | 94.69 | 100.00 | 100.00 | 100.00 | 99.69 | 99.94 |
| Selectivity (%) CO | 0.00 | 0.00 | 0.00 | 0.00 | 0.00 | 0.00 | 0.06 |
| CO2 | 0.00 | 0.00 | 0.00 | 0.00 | 0.00 | 0.00 | 0.00 |
| CH4 | 0.62 | 0.21 | 0.21 | 0.39 | 0.65 | 0.88 | 1.67 |
| C2' | 1.25 | 4.33 | 3.24 | 5.94 | 8.65 | 9.85 | 12.73 |
| C2 | 0.00 | 0.01 | 0.01 | 0.06 | 0.10 | 0.14 | 0.25 |
| C3' | 2.22 | 23.75 | 31.57 | 43.42 | 47.12 | 48.51 | 48.34 |
| C3 | 0.00 | 0.56 | 0.62 | 0.56 | 0.50 | 0.47 | 0.41 |
| C4' | 0.00 | 10.33 | 17.01 | 17.59 | 16.26 | 15.96 | 15.08 |
| i-C4 | 0.00 | 3.56 | 2.38 | 1.01 | 0.54 | 0.00 | 0.00 |
| n-C4 | 0.00 | 0.23 | 0.31 | 0.26 | 0.14 | 0.12 | 0.08 |
| C5' | 0.00 | 3.96 | 2.32 | 1.63 | 1.18 | 0.93 | 0.59 |
| C5 | 0.21 | 6.74 | 6.34 | 5.72 | 4.60 | 4.46 | 4.11 |
| Ethanol | 0.00 | 0.50 | 0.24 | 0.00 | 0.00 | 0.00 | 0.00 |
| Benzene | 0.00 | 0.00 | 0.00 | 0.00 | 0.00 | 0.00 | 0.00 |
| Toluene | 0.00 | 0.44 | 0.57 | 0.00 | 0.08 | 0.54 | 1.03 |
| Xylene | 1.33 | 1.54 | 0.78 | 0.00 | 0.08 | 0.39 | 0.81 |
| Balance | 94.37 | 43.85 | 34.40 | 23.42 | 20.09 | 17.75 | 14.86 |
| (C2' + C3') Yield (C-%) | 0.18 | 26.59 | 34.81 | 49.36 | 55.77 | 58.18 | 61.03 |
| (C2'~C4') Yield (C-%) | 0.18 | 36.37 | 51.82 | 66.95 | 72.03 | 74.09 | 76.10 |

TABLE 9

Effect of Sample 0c on Methanol Conversion Reaction

| | | | | | | | |
|---|---|---|---|---|---|---|---|
| Reaction Time (h) | 5 | 7 | 9 | 11 | 13 | 15 | 17 |
| Reaction Temp. (°C.) | 359 | 399 | 439 | 498 | 539 | 558 | 598 |
| Methanol Conversion (%) | 16.66 | 31.20 | 46.28 | 65.68 | 73.36 | 76.42 | 78.19 |
| Effective Conversion (C-%) | 1.27 | 2.70 | 1.96 | 0.32 | 0.73 | 4.27 | 21.59 |

TABLE 9-continued

| | Effect of Sample 0c on Methanol Conversion Reaction | | | | | | | |
|---|---|---|---|---|---|---|---|---|
| Selec-<br>tivity<br>(%) | CO | 0.00 | 0.00 | 0.00 | 1.24 | 32.10 | 42.50 | 31.27 |
| | $CO_2$ | 0.00 | 0.00 | 0.00 | 0.00 | 0.00 | 1.38 | 1.49 |
| | $CH_4$ | 0.00 | 0.00 | 0.00 | 17.34 | 54.37 | 43.53 | 52.70 |
| | C2' | 0.00 | 0.00 | 0.00 | 2.79 | 7.38 | 3.00 | 2.67 |
| | C2 | 0.00 | 0.00 | 0.00 | 0.00 | 0.00 | 0.96 | 2.55 |
| | C3' | 0.00 | 0.00 | 0.00 | 0.00 | 0.00 | 0.00 | 0.00 |
| | C3 | 0.00 | 0.00 | 0.00 | 0.00 | 0.00 | 0.00 | 0.00 |
| | C4' | 0.70 | 0.00 | 0.00 | 0.00 | 0.00 | 0.00 | 0.00 |
| | i-C4 | 0.00 | 0.00 | 0.00 | 0.00 | 0.00 | 0.00 | 0.00 |
| | n-C4 | 0.00 | 0.66 | 0.00 | 0.00 | 0.00 | 0.00 | 0.05 |
| | C5' | 6.06 | 2.06 | 5.18 | 3.41 | 4.64 | 1.59 | 0.00 |
| | C5 | 1.71 | 0.40 | 1.14 | 3.41 | 1.50 | 0.00 | 0.11 |
| | Ethanol | 0.00 | 0.00 | 0.00 | 0.00 | 0.00 | 0.00 | 0.00 |
| | Benzene | 0.00 | 0.00 | 0.00 | 0.00 | 0.00 | 0.00 | 0.00 |
| | Toluene | 2.41 | 0.00 | 0.00 | 0.00 | 0.00 | 0.00 | 0.00 |
| | Xylene | 89.12 | 96.88 | 11.04 | 16.72 | 0.00 | 6.41 | 0.00 |
| | Balance | 0.00 | 0.00 | 82.64 | 55.11 | 0.00 | 0.00 | 8.79 |
| (C2' + C3') Yield<br>(C-%) | | 0.00 | 0.00 | 0.00 | 0.01 | 0.05 | 0.16 | 0.66 |
| (C2'~C4') Yield<br>(C-%) | | 0.01 | 0.00 | 0.00 | 0.01 | 0.05 | 0.16 | 0.66 |

It will thus be seen that the objects set forth above, and those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A process for preparing a lower olefin comprising the step of carrying out the reaction of methanol and/or dimethyl ether at a temperature of 300°–700° C. under an overall normal atmospheric pressure of 0.1–100 at a weight hourly space velocity of 0.01–20 $hr^{-1}$ in the presence of an aluminosilicate zeolite-type catalyst which contains 0.7 wt.% or more of a calcium-containing compound and 0.7 wt.% or more of a phosphorus-containing compound, respectively.

2. The process as defined in claim 1, wherein said catalyst is a calcium phosphate modified zeolite catalyst which comprises synthetic or natural aluminosilicate zeolite and calcium phosphate mixed with and/or carried on said zeolite.

3. The process according to claim 1 wherein said calcium-containing compound and said phosphorus-containing compound are at least 1.0 weight % calcium and at least 1.0 weight % phosphorus.

4. The process according to claim 1 wherein a molar ratio of calcium to phosphorus in said zeolite is between 0.3 to 1.7.

5. The process according to claim 1 wherein said zeolite catalyst is calcinated in an air or nitrogen stream.

6. The process according to claim 1 wherein said weight hourly space velocity is between 1 $hr^{-1}$–10 $hr^{-1}$.

7. The process according to claim 1 wherein said pressure is 0.5–10 normal atmospheric pressure.

8. The process according to claim 1 wherein said starting materials are diluted by water vapor or an inert gas and fed onto said zeolite catalyst.

* * * * *